United States Patent
Shi

(10) Patent No.: US 11,406,914 B2
(45) Date of Patent: Aug. 9, 2022

(54) SYSTEMS AND METHODS FOR CANNABIS CBD EXTRACTION

(71) Applicant: Pacific Import Manufacturing, Inc., City of Industry, CA (US)

(72) Inventor: Minyu Shi, Tianjin (CN)

(73) Assignee: Pacific Import Manufacturing, Inc., City of Industry, CA (US)

( * ) Notice: Subject to any disclaimer, the term of this patent is extended or adjusted under 35 U.S.C. 154(b) by 82 days.

(21) Appl. No.: 16/932,300

(22) Filed: Jul. 17, 2020

(65) Prior Publication Data
US 2022/0016545 A1    Jan. 20, 2022

(51) Int. Cl.
| | |
|---|---|
| *B01D 11/02* | (2006.01) |
| *B01D 3/10* | (2006.01) |
| *C07C 39/08* | (2006.01) |
| *A61K 36/18* | (2006.01) |
| *A61K 36/185* | (2006.01) |

(52) U.S. Cl.
CPC ........ *B01D 11/0284* (2013.01); *A61K 36/185* (2013.01); *B01D 3/10* (2013.01); *B01D 11/0207* (2013.01); *B01D 11/0288* (2013.01); *B01D 11/0296* (2013.01); *C07C 39/08* (2013.01)

(58) Field of Classification Search
CPC .. B01D 11/0284; B01D 3/10; B01D 11/0207; B01D 11/0288; B01D 11/0296; B01D 1/00; B01D 3/00; B01D 11/0269; B01D 11/0273; B01D 11/0292; B01D 19/00; B01D 19/0068; B01D 21/00; B01D 21/262; B01D 36/00; B01D 36/001; B01D 36/04; B01D 37/00; A61K 36/18; A61K 36/185; C07C 39/08; C07C 37/004; C07C 37/685; C07C 37/70; C07C 37/72; C07C 37/74; C07C 37/82
See application file for complete search history.

(56) References Cited

U.S. PATENT DOCUMENTS

| | | | |
|---|---|---|---|
| 9,937,218 B2 | 4/2018 | Towle | |
| 9,994,464 B2 | 6/2018 | Dietz | |
| 10,557,105 B1 * | 2/2020 | Tran | .................. C11B 1/104 |
| 10,919,828 B1 * | 2/2021 | Roa-Espinosa | ......... C07C 37/50 |
| 2010/0008835 A1 * | 1/2010 | Birdwell, Jr. | ............ B01J 14/00 422/209 |
| 2020/0016508 A1 * | 1/2020 | Hari | ................... B01D 15/08 |
| 2020/0122052 A1 * | 4/2020 | Tucker | ................. B01D 3/001 |
| 2020/0172503 A1 * | 6/2020 | Oroskar | ............ B01D 15/1821 |
| 2020/0199055 A1 * | 6/2020 | Jansen | ................. C07D 311/78 |
| 2020/0246404 A1 * | 8/2020 | Yucel | ................... A61K 36/185 |
| 2020/0361841 A1 * | 11/2020 | Stone | ................... C07C 37/004 |
| 2021/0094929 A1 * | 4/2021 | Tegen | ............... B01D 11/0269 |
| 2021/0268401 A1 * | 9/2021 | Wirtz | ................ B01D 11/0273 |

* cited by examiner

*Primary Examiner* — Joseph W Drodge
(74) *Attorney, Agent, or Firm* — Sheridan Ross P.C.

(57) ABSTRACT

Systems and methods for extracting a compound of interest from plant material, such as acannabidiol (CBD) from cannabis, are provided. Particularly, the disclosed systems and methods utilize a crude oil to separate water, fats, and proteins prior to preparation of a CBD distillate. The systems and methods are operable with conventional solvents containing between about 5 wt % and about 8 wt % water.

19 Claims, 10 Drawing Sheets

SYSTEMS AND METHODS FOR CANNABIS CBD EXTRACTION

FIELD OF THE INVENTION

This invention relates generally to systems and methods for extracting cannabidiol (CBD) from cannabis, and particularly to systems and methods that utilize a crude oil to separate water, fats, and proteins prior to preparation of a CBD distillate.

BACKGROUND OF THE INVENTION

At present, the most efficient methods for extracting cannabidiol (CBD) from cannabis plants are solvent extraction processes, in which the cannabis biomass is contacted with a liquid solvent. Ethanol is widely considered the most effective solvent for such processes and is by far the most commonly used. However, pure (99% purity or higher) ethanol is very expensive and tightly regulated by many governments, and is thus extremely difficult to obtain in quantities sufficient for industrial-scale applications (3,000 to 5,000 gallons). As a result, most skilled artisans use a mixture of ethanol and water, typically comprising 5% to 8% water, as the solvent in CBD solvent extraction processes.

The presence of water in CBD extraction solvents presents several drawbacks. Most significantly, when cannabis biomass is contacted with an aqueous solvent, fats and hydrophilic proteins in the cannabis biomass are solubilized in the water. When the solvent is subsequently heated, as most separation processes require, the proteins in the solvent solidify, thus fouling process equipment and requiring frequent shutdown and cleaning of the extraction system.

There is thus a need in the art for systems and methods for extracting CBD from cannabis that avoid or prevent fouling and clogging of the process equipment by proteins and other impurities present in the solvent after extraction. It is further advantageous for such systems and methods to be compatible with currently known, inexpensive, and/or widely available solvents, e.g. ethanol/water mixtures.

SUMMARY OF THE INVENTION

It is one aspect of the present invention to provide a method for separating a first organic substance from a second organic substance in an aqueous solution or suspension, comprising (a) providing the aqueous solution or suspension, the aqueous solution or suspension comprising the first and second organic substances; (b) forming a first phase and a second phase from the aqueous solution or suspension by at least one of (i) contacting the aqueous solution or suspension with at least one of a liquid separating agent and a solid separating agent, and (ii) at least one of centrifugation, filtration, and sedimentation of the aqueous solution or suspension; and (c) removing one of the first phase and the second phase to a vessel, wherein the first organic substance comprises at least one of a cannabinoid and a terpene, wherein the second organic substance comprises at least one of a protein and a lipid, wherein the first phase comprises at least most of the first organic substance present in the aqueous solution or suspension, wherein the second phase comprises at least most of the second organic substance present in the aqueous solution or suspension, and wherein the first and second phases are substantially immiscible.

In embodiments, the first organic substance may comprise a cannabinoid. The cannabinoid may, but need not, be cannabidiol.

In embodiments, the aqueous solution or suspension may originate from an ethanol extraction process for extraction of the first organic substance from cannabis plant material. The method may, but need not, further comprise obtaining a solid fraction of the second phase by at least one of drying the second phase and filtering the second phase; and recycling the solid fraction of the second phase to the ethanol extraction process.

In embodiments, the method may further comprise providing the first phase to a distillation process for producing a distillate of the first organic substance.

In embodiments, the first phase may comprise at least about 75% of the first organic substance present in the aqueous solution or suspension.

In embodiments, at least one step may be carried out at a temperature of no more than about 75° C.

It is another aspect of the present invention to provide a method for preparing a purified cannabis extract, comprising (a) contacting cannabis plant material with a liquid mixture of ethanol and water to form a raw extract comprising ethanol, water, at least one cannabinoid or terpene, and at least one protein or lipid; (b) recovering at least most of the ethanol from the raw extract to form a crude cannabis oil; (c) forming a first phase and a second phase from the crude cannabis oil by at least one of (i) contacting the aqueous solution or suspension with at least one of a liquid separating agent and a solid separating agent, and (ii) at least one of centrifugation, filtration, and sedimentation of the aqueous solution or suspension; (d) removing one of the first phase and the second phase to a vessel; and (e) distilling the first phase to form the purified cannabis extract, wherein the first phase comprises at least most of the at least one cannabinoid or terpene present in the crude cannabis oil, wherein the second phase comprises at least most of the at least one protein or lipid present in the crude cannabis oil, and wherein the first and second phases are substantially immiscible.

In embodiments, the at least one cannabinoid or terpene may comprise cannabidiol.

In embodiments, the method may further comprise obtaining a solid fraction of the second phase by at least one of drying the second phase and filtering the second phase; and recycling the solid fraction of the second phase to step (b) as part of the raw extract or to step (c) as part of the crude cannabis oil.

In embodiments, the first phase may comprise at least about 75% of the cannabinoid or terpene present in the crude cannabis oil.

In embodiments, at least one of steps (a), (b), (c), and (d) may be carried out at a temperature of no more than about 75° C.

In embodiments, the purified cannabis extract may be substantially free of proteins and lipids.

In embodiments, the purified cannabis extract may comprise at least about 70 wt % cannabinoids and terpenes. The purified cannabis extract may, but need not, comprise at least about 70 wt % cannabidiol.

It is another aspect of the present invention to provide a liquid composition, comprising at least about 70 wt % cannabinoids and terpenes and being substantially free of proteins and lipids.

In embodiments, the liquid composition may comprise at least about 70 wt % cannabidiol. The liquid composition may, but need not, be substantially free of cannabidiolic acid.

In embodiments, the liquid composition may be produced by a method comprising (a) providing the aqueous solution or suspension, the aqueous solution or suspension comprising the first and second organic substances; (b) forming a first phase and a second phase from the aqueous solution or suspension by at least one of (i) contacting the aqueous solution or suspension with at least one of a liquid separating agent and a solid separating agent, and (ii) at least one of centrifugation, filtration, and sedimentation of the aqueous solution or suspension; (c) removing one of the first phase and the second phase to a vessel; and (d) distilling the first phase, wherein the first organic substance comprises at least one of a cannabinoid and a terpene, wherein the second organic substance comprises at least one of a protein and a lipid, wherein the first phase comprises substantially all of the first organic substance present in the aqueous solution or suspension and is substantially free of the second organic substance, wherein the second phase comprises substantially all of the second organic substance present in the aqueous solution or suspension and is substantially free of the first organic substance, and wherein the first and second phases are substantially immiscible.

In embodiments, the liquid composition may be produced by a method comprising (a) contacting cannabis plant material with a liquid mixture of ethanol and water to form a raw extract comprising ethanol, water, at least one cannabinoid or terpene, and at least one protein or lipid; (b) recovering at least most of the ethanol from the raw extract to form a crude cannabis oil; (c) forming a first phase and a second phase from the crude cannabis oil by at least one of (i) contacting the aqueous solution or suspension with at least one of a liquid separating agent and a solid separating agent, and (ii) at least one of centrifugation, filtration, and sedimentation of the aqueous solution or suspension; (d) removing one of the first phase and the second phase to a vessel; and (e) distilling the first phase to form the purified cannabis extract, wherein the first phase comprises at least most of the at least one cannabinoid or terpene present in the crude cannabis oil, wherein the second phase comprises at least most of the at least one protein or lipid present in the crude cannabis oil, and wherein the first and second phases are substantially immiscible.

It is another aspect of the present invention to provide a system for preparing a purified plant extract, comprising a centrifugal separation unit, comprising at least one centrifugal separator, configured to receive plant material and a liquid solvent comprising ethanol, mix the plant material and the liquid solvent to form a slurry, and centrifuge the slurry in the centrifugal separator to separate the slurry into a solid residue and a raw extract, wherein the raw extract comprises at least one compound of interest and at least most of the liquid solvent; a filtration unit, comprising a filter assembly, configured to filter the raw extract to remove entrained solid plant material from the raw extract; a concentration unit, comprising an evaporator configured to receive the raw extract and heat the raw extract to remove at least most of the solvent therefrom by evaporation to thereby form a concentrated extract; a settling unit, comprising at least one settling vessel, configured to receive the concentrated extract and cause sedimentation of at least one impurity therefrom; a decarboxylation and degassing unit, comprising an atmosphere heating vessel and a vacuum heating vessel, wherein the atmosphere heating vessel is configured to receive the concentrated extract from the settling unit and heat the concentrated extract under approximately ambient or atmospheric pressure to decarboxylate at least a portion of the concentrated extract to form a decarboxylated oil, wherein the vacuum heating vessel is configured to receive the decarboxylated oil from the atmosphere heating vessel and heat the decarboxylated oil under sub-atmospheric pressure to form a winterized oil; and a short-path distillation unit, comprising at least one short-path distillation apparatus configured to receive the winterized oil from the decarboxylation and degassing unit and distill the winterized oil to form the purified plant extract.

In embodiments, the plant material may be a cannabis plant material.

In embodiments, the at least one compound of interest may comprise at least one cannabinoid or terpene. The at least one compound of interest may, but need not, comprise cannabidiol.

In embodiments, a content of the at least one compound of interest in the purified plant extract may be at least about 70% by weight.

In embodiments, the liquid solvent may consist essentially of (i) between about 92 and about 95 wt % ethanol and (ii) water.

In embodiments, the at least one impurity may comprise at least one protein or lipid.

In embodiments, the system may further comprise a rectification unit, configured to receive evaporated solvent from the concentration unit and recover the solvent for recycle to at least one other unit of the system.

It is another aspect of the present invention to provide a method for preparing a purified plant extract, comprising (a) contacting plant material with a liquid solvent containing ethanol to form a slurry; (b) centrifuging the slurry to form a raw extract comprising at least one compound of interest and at least most of the liquid solvent; (c) filtering the raw extract to remove entrained solid plant material from the raw extract; (d) concentrating the raw extract by heating the raw extract to remove at least most of the solvent therefrom by evaporation to thereby form a concentrated extract; (e) precipitating a sediment comprising at least one impurity from the concentrated extract; (f) decarboxylating the concentrated extract by heating the concentrated extract under approximately ambient or atmospheric pressure to form a decarboxylated oil; (g) heating the decarboxylated oil under sub-atmospheric pressure to form a winterized oil; and (h) distilling the winterized oil by short-path distillation to form the purified plant extract.

In embodiments, the plant material may be a cannabis plant material.

In embodiments, the at least one compound of interest may comprise at least one cannabinoid or terpene. The at least one compound of interest may, but need not, comprise cannabidiol.

In embodiments, a content of the at least one compound of interest in the purified plant extract may be at least about 70% by weight.

In embodiments, the liquid solvent may consist essentially of (i) between about 92 and about 95 wt % ethanol and (ii) water.

In embodiments, the at least one impurity may comprise at least one protein or lipid.

In embodiments, the method may further comprise rectifying the solvent evaporated in step (d) for recycle to at least one of steps (a), (b), and (c).

For purposes of further disclosure and to comply with applicable written description and enablement requirements, the following references generally relate to systems and methods for extracting a compound or compounds of interest from plant material and/or separating organic compounds and impurities from an aqueous solution or suspension, and are hereby incorporated by reference in their entireties:

U.S. Pat. No. 9,937,218, entitled "Systems and methods for cannabinoid and terpene extraction and purification," issued 10 Apr. 2018 to Towle.

U.S. Pat. No. 9,994,464, entitled "Method and devices for de-emulsifying and complexing organic compounds in emulsions," issued 12 Jun. 2018 to Dietz.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Figure 1:
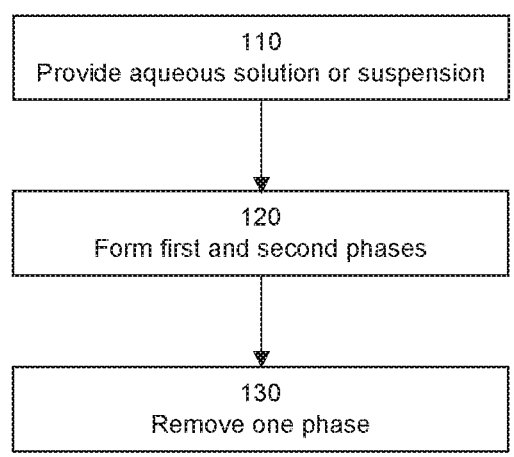
FIG. 1 is a process flow diagram of a method for separating a first organic substance from a second organic substance in an aqueous solution or suspension, according to embodiments of the present invention.

The accompanying drawings are incorporated into and form a part of the specification to illustrate several examples of the present disclosure. The drawings are not to be construed as limiting the disclosure to only the illustrated and described examples.

DETAILED DESCRIPTION OF THE INVENTION

As used herein, unless otherwise specified, the term "cannabis" refers to any plant in the genus *Cannabis*.

As used herein, unless otherwise specified, the term "hemp" refers to cannabis plant material containing no more than about 0.3% tetrahydrocannabinol by weight.

As used herein, unless otherwise specified, the term "plant material" refers to whole plants and/or parts of plants that contain one or more compounds to be extracted, including but not limited to aerial parts, leaves, stems, flowering heads, fruits, and/or roots. "Plant material" may be freshly harvested plants or parts of plants, plants or parts of plants that have been subjected to one or more pre-treatment steps (e.g. drying, removal of debris, etc.), and/or plants or parts of plants that have been frozen or pelletized.

Before any embodiments of the disclosure are explained in detail, it is to be understood that the disclosure is not limited in its application to the details of construction and the arrangement of components set forth in the following description or illustrated in the following drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example,"

"by way of example," "e.g.," "such as," or similar language) is not intended to and does not limit the scope of the present disclosure.

Although the following description generally refers to embodiments in which the methods and systems of the invention are employed to extract, e.g., cannabinoids from, e.g., cannabis, it is to be expressly understood that the present invention may be suitably applied to any plant or other biomass material to extract any compound that may be obtained by distillation. By way of non-limiting example, the present invention may be employed to extract essential oils or other volatile compounds from spices, fruits, flowers, or any other suitable plant material, as such embodiments are within the scope of the present invention.

One advantage of methods and systems of the present invention is that cannabis extracts produced by the present invention may contain a blend of cannabinoids in approximately the same proportion as are present in the raw cannabis plant material. In other words, little or no fractionation of cannabinoids may be observed so a "Full Spectrum" product is produced that reflects the cannabinoid profile of the feedstock.

Crude oils produced from conventional ethanol extraction processes generally comprise at least some lipids and proteins dissolved in water. Additionally or alternatively, such crude oils may comprise carboxylic acids, phospholipids, glycolipids, glyceroglycolipids, phenols, sterols, squalene, plant dyes, such as chlorophylls and carotenes, sinapines, peptides, proteins, carbohydrates, lipoproteins, waxes and/or fatty alcohols. Thereby, the carboxylic acids, phospholipids, glycolipids, glyceroglycolipids, phenols, sterols, squalene, plant dyes, such as chlorophylls and carotenes, sinapines, peptides, proteins, carbohydrates, lipoproteins, flavoring agents, waxes and/or fatty alcohols may be present individually or as a mixture in the aqueous solutions or suspensions, e.g., for example, as a mixture of peptides, sterols, and carbohydrates or a mixture of glycolipids and phospholipids. Aqueous solutions and suspensions suitable for refinement according to the present invention may also contain phospholipids, glycolipids, glyceroglycolipids, phenols, sterols, squalene, flavorings, vegetable dyes, such as chlorophylls and carotenoids, and/or sinapines apart from carboxylic acids.

According to the present invention, proteins, lipids, and similar organic substances that may be considered impurities or otherwise undesirable may be separated from cannabinoids, terpenes, and other compounds of interest by separating crude aqueous solutions or suspensions, e.g. crude extracts or oils of cannabis, into two distinct phases, one phase being relatively rich in the cannabinoids/terpenes and relatively poor in the proteins, lipids, etc., and the other phase being relatively poor in the cannabinoids/terpenes and relatively rich in the proteins, lipids, etc. This phase separation may be accomplished by any one or more of several means. By way of first non-limiting example, phase separation may be achieved by chemical means, e.g. by contacting the aqueous solution or suspension with a liquid or solid separating agent. By way of second non-limiting example, phase separation may be achieved by physical means, e.g. by centrifugation, filtration, and/or sedimentation of the aqueous solution or suspension.

Chemical separating agents in any form, e.g. solids, powders, aqueous dispersions of solids, etc., can be added to crude extracts and oils as disclosed in the methods described herein. In embodiments, the addition may be carried out by mixing, and/or at a maximum temperature of about 75° C., and/or with a laminar agitator.

Aqueous extraction mixtures suitable for separation according to the present invention may contain, besides the above-mentioned proteins, lipids, and carboxylic acids, phospholipids, glycolipids, glyceroglycolipids, phenols, sterols, squalenes, and/or vegetable dyes, such as chlorophylls and carotenes. These and other similar organic substances may likewise be separated from cannabinoids, terpenes, and/or other compounds of interest according to the present invention.

Methods of the present invention may or may not include adjusting the pH of the crude plant extract or oil or other aqueous solution or suspension of interest. In some embodiments, the pH of one or both phases after separation may be approximately equal to that of the initial aqueous solution, i.e. before separation. Methods of the present invention may thus be useful to treat acidic solutions or suspensions, basic solutions or suspensions, and/or neutral solutions or suspensions.

The present invention may be useful to separate proteins and/or lipids from other compounds of interest regardless of the physical nature of the initial aqueous suspension or solution from which the compounds are to be separated. By way of first non-limiting example, the aqueous solution or suspension may be a true solution, i.e. the protein(s) and/or lipid(s) may be dissolved throughout an aqueous solvent. By way of second non-limiting example, the aqueous solution or suspension may be a colloid, i.e. the protein(s) and/or lipid(s) may be dispersed throughout an aqueous liquid dispersion medium as solid or liquid particles that are too small for sedimentation, or sufficiently small that the sedimentation time is impractically long. By way of third non-limiting example, the aqueous solution or suspension may be a non-colloidal suspension, i.e. the protein(s) and/or lipids may be dispersed throughout an aqueous liquid dispersion medium as macroscopic solid or liquid particles.

Particularly, the inventive process is suitable for aqueous solutions or suspensions that originate from solvent extraction processes for extracting one or more compounds of interest from solid material, and especially from ethanol extraction processes for extracting one or more compounds of interest from plant material, e.g. cannabis plant material. As described throughout this disclosure, crude extracts resulting from such processes may contain, in addition to a compound of interest (e.g. a cannabinoid or terpene), water and water-soluble proteins and lipids extracted from the plant material. Typically, such extracts must be distilled to provide a purified extract, but heating of the crude extract may result in solidification or sedimentation of the proteins and/or lipids, which may foul process equipment. By separating a phase containing organic impurities such as proteins and lipids from a phase containing the compound of interest, the present invention greatly mitigates the need to unclog or clean process equipment, resulting in greater process uptime and reduced cost.

In embodiments, the methods of the present invention result in the formation of an aqueous phase comprising protein(s) and/or lipid(s) that can be re-processed or further processed to separate residual compounds of interest, e.g. cannabinoids or terpenes, remaining in such phase. Particularly, the protein/lipid phase resulting from separations according to the present invention can be filtered and/or dried to produce a solid fraction, which may then be subjected to an extraction process, e.g. recycled to an earlier solvent extraction process. In this way, methods of the present invention are suitable not only to avoid fouling of process equipment in solvent extraction/distillation processes for purification of compounds of interest, but also to improve the overall recovery of the compounds of interest in such processes. Such filtration and/or drying may, in some embodiments, also result in a relatively high-purity liquid fraction of water, which may likewise be useful in other processes and/or steps.

One advantage of the present invention relative to conventional methods is that both the compound(s) of interest, e.g. cannabinoids and terpenes, and the protein(s) and lipid(s) to be separated from the compounds of interest may be obtained without significant physical or chemical degradation or decomposition. More specifically, embodiments of the methods of the present invention do not require exposure of sensitive organic compounds to extreme temperatures or pressures, or to strong acids, bases, or other chemicals that may degrade, cause hydrolysis of, or otherwise damage the compound(s) of interest, protein(s), or lipid(s); in fact, it may in many embodiments be preferable to carry out the methods of the present invention at moderate temperatures (e.g. between about 0° C. and about 100° C., between about 15° C. and 75° C., between about 20° C. and about 50° C., or between about 25° C. and about 35° C., or in some embodiments no more than about 75° C.). As a result, either phase, or both phases, can be further processed to yield a safe and high-purity product, e.g. a cannabis distillate comprising at least about 70% cannabinoids and/or terpenes by weight. Proteins and lipids separated from the aqueous solution or suspension may likewise be in a chemically and physically intact and/or neutral form suitable for further use, e.g. in foods, cosmetic products, pharmaceuticals, flavoring agents, etc.

Neutral lipids may present particular separation challenges because they typically cannot be separated from aqueous solutions or suspensions by physical means such as centrifugation. By the practice of the present invention, separation of the neutral lipids present in aqueous solutions and suspensions can be obtained, e.g., by increasing a separation temperature and inducing aggregation of the neutral lipids. In this way, the methods of the present invention enable the separation of neutral fats from aqueous solutions and suspensions, either from compounds of interest or from proteins and other lipids.

Embodiments of the present invention may advantageously result in the formation of a phase containing a relatively high proportion of water and a phase containing a relatively low proportion of water. Particularly, in embodiments, the methods of the present invention may produce a water-poor phase that is rich in the compound(s) of interest, e.g. cannabinoids and terpenes, and a water-rich phase that is rich in impurities, e.g. protein(s) and lipids. The water-poor phase can then be further purified, e.g. by distillation or other temperature- or pressure-intensive methods, without causing fouling or clogging of process equipment, while the water-rich phase can be recycled, purged, or further purified by any of several well-known means, such as the use of decanters, separators, filter technology, vacuum drying, inert gas drying, heating, etc. to separate organic aggregates, e.g. proteins and lipids. In addition, the shelf life of the compound(s) of interest in the water-poor phase may be extended, due to the avoidance of physical contact with impurities and water for an extended period, and the proteins and lipids may likewise be suitable for later use in other products or processes.

Embodiments of the present invention allow more efficient and effective separation of compounds of interest, e.g. cannabinoids and terpenes, from protein and lipid impurities than conventional separation methods. By way of first non-limiting example, methods of the present invention may allow for formation of a cannabinoid- and/or terpene-rich phase that comprises at least about 50 wt %, at least about 55 wt %, at least about 60 wt %, at least about 65 wt %, at least about 70 wt %, at least about 75 wt %, at least about 80 wt %, at least about 85 wt %, at least about 90 wt %, at least about 95 wt %, at least about 96 wt %, at least about 97 wt %, at least about 98 wt %, or at least about 99 wt % of the cannabinoids and/or terpenes present in the input aqueous solution or suspension. By way of second non-limiting example, methods of the present invention may allow for formation of a protein- and/or lipid-rich phase that comprises at least about 50 wt %, at least about 55 wt %, at least about 60 wt %, at least about 65 wt %, at least about 70 wt %, at least about 75 wt %, at least about 80 wt %, at least about 85 wt %, at least about 90 wt %, at least about 95 wt %, at least about 96 wt %, at least about 97 wt %, at least about 98 wt %, or at least about 99 wt % of the proteins and/or lipids present in the input aqueous solution or suspension. By way of third non-limiting example, methods of the present invention may allow for formation of a protein- and/or lipid-poor phase that comprises no more than about 50 wt %, no more than about 45 wt %, no more than about 40 wt %, no more than about 35 wt %, no more than about 30 wt %, no more than about 25 wt %, no more than about 20 wt %, no more than about 15 wt %, no more than about 10 wt %, no more than about 5 wt %, no more than about 4 wt %, no more than about 3 wt %, no more than about 2 wt %, or no more than about 1 wt % of the proteins and/or lipids present in the input aqueous solution or suspension. By way of fourth non-limiting example, methods of the present invention may allow for formation of a cannabinoid- and/or terpene-poor phase that comprises no more than about 50 wt %, no more than about 45 wt %, no more than about 40 wt %, no more than about 35 wt %, no more than about 30 wt %, no more than about 25 wt %, no more than about 20 wt %, no more than about 15 wt %, no more than about 10 wt %, no more than about 5 wt %, no more than about 4 wt %, no more than about 3 wt %, no more than about 2 wt %, or no more than about 1 wt % of the cannabinoids and/or terpenes present in the input aqueous solution or suspension.

In some embodiments, separation of proteins and/or lipids from compounds of interest may be effectuated by initiating aggregation and subsequent sedimentation of proteins and/or lipids from the aqueous solutions or suspension, thus leaving behind a phase containing the compound of interest and having a diminished content of proteins and/or lipids. In these and other embodiments, separation of proteins and/or lipids from compounds of interest may be effectuated by initiating separation of the solution into a water-poor or hydrophobic phase, which preferentially includes oily, hydrophobic, or poorly water-soluble contents of the aqueous solution or suspension (e.g. cannabinoids, terpenes, etc.), and a water-rich or hydrophilic phase, which preferentially includes water and hydrophilic, amphiphilic, or highly water-soluble contents of the aqueous solution or suspension (e.g. proteins, lipids, etc.). In some embodiments, it may be possible to decant or otherwise separate the water of the protein- or lipid-rich phase from the proteins and lipids, e.g. when the aqueous solution or suspension is separated into two liquid phases and the proteins and lipids subsequently aggregate and precipitate out of a water-rich liquid phase. Alternatively, solid or semi-solid aggregates of proteins, lipids, and/or other impurities may, standing alone, constitute all or a majority of the mass or volume of a phase, in which case it may be possible to separate the entire liquid contents of the reactor or vessel in which separation is being carried out, e.g. by means of a sieve or filter. In any of these embodiments, either phase may be washed or further processed to improve fractionation still further.

Referring now to FIG. 1, a method 100 for separating a first organic substance from a second organic substance in an aqueous solution or suspension is illustrated, according to embodiments of the present invention. In the embodiment illustrated in FIG. 1, the method 100 comprises a providing step 110, a forming step 120, and a removing step 130.

In the providing step 110 of the method 100, an aqueous solution or suspension, comprising a first organic substance and a second organic substance, is provided. In embodiments, the first organic substance generally includes at least one cannabinoid, at least one terpene, or a combination or mixture thereof, and the second organic substance generally includes at least one protein, at least one lipid, or a combination or mixture thereof, but it is to be expressly understood that various other organic substances may be suitable, as described throughout this disclosure. In some preferred embodiments, the first organic substance may comprise cannabidiol (CBD), and the second organic substance may comprise a combination or mixture of at least partially water-soluble, water-miscible, and/or hydrophilic protein(s) and/or lipids, particularly protein(s) and/or lipid(s) susceptible to solidification (and thus fouling or clogging of process equipment) upon heating. In many embodiments, the aqueous solution may be a crude cannabis extract, and particularly the product of an ethanol extraction process for extraction of a compound of interest (i.e. the first organic substance or a component thereof) from cannabis plant material.

In the forming step 120 of the method 100, the aqueous solution or suspension is separated into a first phase and a second phase by any suitable means. By way of first non-limiting example, the first and second phases may be formed by contacting the aqueous solution or suspension with a solid separating agent and/or a liquid separating agent; in embodiments, a liquid separating agent may be a liquid (e.g. aqueous) solution or dispersion of a solid separating agent (e.g. a copper salt, a calcium salt, a sodium salt, a magnesium salt, silica, etc.). By way of second non-limiting example, the first and second phases may be formed by centrifuging the aqueous solution or suspension. By way of a third non-limiting example, the first and second phases may be formed by filtering the aqueous solution or suspension. By way of a fourth non-limiting example, the first and second phases may be formed by causing or triggering sedimentation of solid particles (e.g. comprising protein(s) and/or lipids) from the aqueous solution or suspension. Generally, the first phase resulting from forming step 120 is a first substance-rich phase, e.g. a cannabinoid- and/or terpene-rich phase (e.g. comprising at least most, and in embodiments at least 75%, of cannabinoids and/or terpenes in the aqueous solution or suspension), and the second phase resulting from forming step 120 is a protein- and/or lipid-rich phase (e.g. comprising at least most of proteins and/or lipids in the aqueous solution or suspension). Typically, the first and second phases may be substantially immiscible to facilitate removing step 130.

In the removing step 130 of the method 100, one of the first and second phases formed in forming step 120 is removed to a vessel separate from that in which forming step 120 is carried out. By way of first non-limiting example, the first phase may be skimmed or otherwise removed from a surface of the second phase where the first and second phases are liquids and the first phase is less dense than the second phase. By way of second non-limiting example, the second phase may be filtered or precipitated from the first phase where the first phase is liquid and the second phase is solid or mostly solid.

The method 100 may optionally include any one or more additional steps not illustrated in FIG. 1. By way of first non-limiting example, the second phase (i.e. the protein- and/or lipid-rich phase) can be filtered and/or dried, and the second phase (and/or a solid fraction thereof) can be recycled to an ethanol extraction process. By way of second non-limiting example, the first phase can be provided to a distillation process for producing a distillate or purified extract, e.g. a purified cannabinoid extract.

In many embodiments, it may be preferable for the steps of the method 100 to be carried out at approximately ambient temperatures, or at only slightly elevated temperatures. Particularly, it may be preferable to ensure that the steps of the method 100 are carried out at temperatures below those at which proteins and/or lipids of the aqueous solution or suspension may solidify, e.g. no more than about 75° C.

Figure 2:
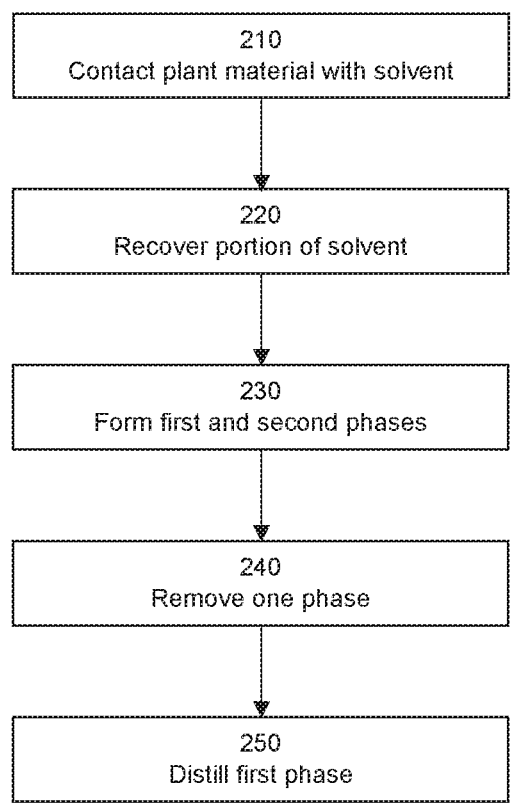
FIG. 2 is a process flow diagram of a method for preparing a purified cannabis extract, according to embodiments of the present invention.

Referring now to FIG. 2, a method for preparing a purified plant extract is illustrated, according to embodiments of the present invention. In the embodiment illustrated in FIG. 2, the method 200 comprises a contacting step 210, a recovering step 220, a forming step 230, a removing step 240, and a distilling step 250.

In the contacting step 210 of the method 200, plant material is subjected to a solvent extraction process, and in particular embodiments an ethanol extraction process, by being contacted with a liquid solvent (e.g. a mixture of ethanol and water). As a result of contacting step 210, a raw extract is produced; the raw extract typically comprises the solvent, a compound or compounds of interest (e.g. cannabinoids and/or terpenes, including but not limited to cannabidiol), and proteins and/or lipids soluble in the solvent or a component thereof.

In the recovering step 220 of the method 200, the solvent or a portion thereof (e.g. ethanol) is removed from the raw extract and optionally recycled to contacting step 210. Removal and recovery of at least a portion of the solvent generally improves the efficiency of subsequent processing steps and results in a purer finished extract.

In the forming step 230 of the method 200, the crude oil is separated into a first phase and a second phase by any suitable means. By way of first non-limiting example, the first and second phases may be formed by contacting the crude oil with a solid separating agent and/or a liquid separating agent; in embodiments, a liquid separating agent may be a liquid (e.g. aqueous) solution or dispersion of a solid separating agent (e.g. a copper salt, a calcium salt, a sodium salt, a magnesium salt, silica, etc.). By way of second non-limiting example, the first and second phases may be formed by centrifuging the crude oil. By way of third non-limiting example, the first and second phases may be formed by filtering the crude oil. By way of fourth non-limiting example, the first and second phases may be formed by causing or triggering sedimentation of solid particles (e.g. comprising protein(s) and/or lipids) from the crude oil. Generally, the first phase resulting from forming step 230 is a first substance-rich phase, e.g. a cannabinoid- and/or terpene-rich phase (e.g. comprising at least most, and in embodiments at least 75%, of cannabinoids and/or terpenes in the aqueous solution or suspension, and having a low proportion of proteins and/or lipids), and the second phase resulting from forming step 230 is a protein- and/or lipid-rich phase (e.g. comprising at least most of proteins and/or lipids in the aqueous solution or suspension, and having a low proportion of substances of interest such as cannabinoids and/or terpenes). Typically, the first and second phases may be substantially immiscible to facilitate removing step 240.

In the removing step 240 of the method 200, one of the first and second phases formed in forming step 230 is removed to a vessel separate from that in which forming step 230 is carried out. By way of first non-limiting example, the first phase may be skimmed or otherwise removed from a surface of the second phase where the first and second phases are liquids and the first phase is less dense than the second phase. By way of second non-limiting example, the second phase may be filtered or precipitated from the first phase where the first phase is liquid and the second phase is solid or mostly solid.

In the distilling step 250 of the method 200, the first phase, i.e. the phase containing the compound or compounds of interest (e.g. cannabinoids and/or terpenes), is distilled to further purify the first phase and produce a purified extract.

The method 200 may optionally include any one or more additional steps not illustrated in FIG. 2. By way of non-limiting example, the second phase (i.e. the protein- and/or lipid-rich phase) can be filtered and/or dried, and the second phase (and/or a solid fraction thereof) can be recycled to recovering step 220 and/or forming step 230.

In many embodiments, it may be preferable for at least one of, and in some embodiments all of, the contacting step 210, the recovering step 220, the forming step 230, and the removing step 240 to be carried out at approximately ambient temperatures, or at only slightly elevated temperatures. Particularly, it may be preferable to ensure that at least one of these steps of the method 200 is carried out at temperatures below those at which proteins and/or lipids of the aqueous solution or suspension may solidify, e.g. no more than about 75° C.

The method 200 may be suitable to obtain a cannabis plant extract having a high proportion of cannabinoids, and in particular a high proportion of cannabidiol. Typically, the cannabinoid content of the purified extract may be at least about 70 wt %, and in some embodiments up to about 80 wt %. The purified extract may be substantially free of proteins and/or lipids, or may have a significantly lower content of proteins and/or lipids relative to cannabis plant extracts obtained by conventional methods.

Figure 3:
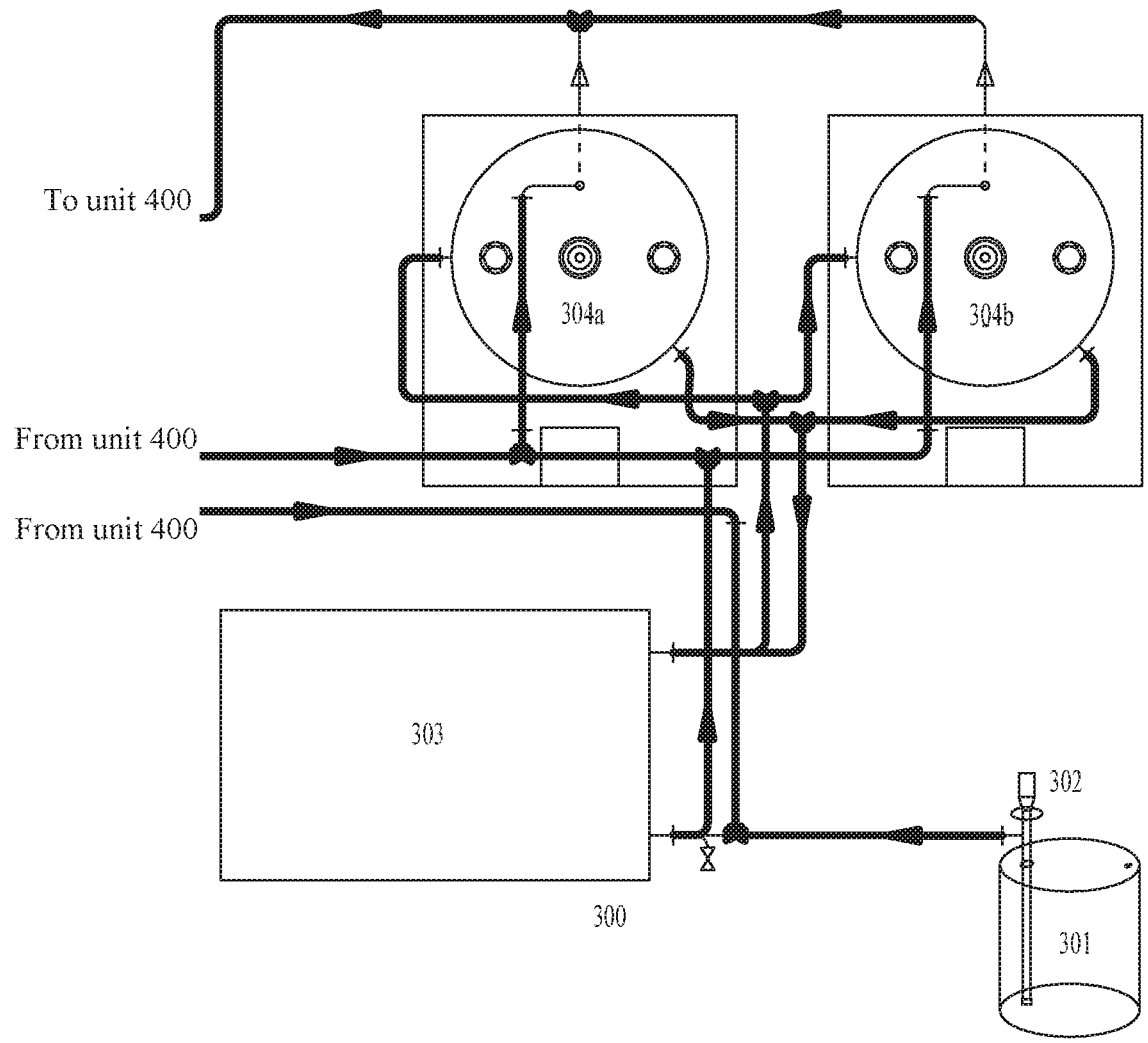
FIG. 3 is an illustration of a centrifugal separation unit of a system for preparing a purified cannabis extract, according to embodiments of the present invention.

Referring now to FIG. 3, a centrifugal separation unit 300 of a system for preparing a purified cannabis extract, according to embodiments of the present invention, comprises an alcohol tank 301, an alcohol pump 302, an optional refrigerator 303, and at least one centrifugal separator 304 (in this case two centrifugal separators 304*a*,*b*). As illustrated in FIG. 3, ethanol is injected by the alcohol pump 302 from the alcohol tank 301 into either the optional refrigerator 303, the centrifugal separator(s) 304, or both; most typically, at least a portion of ethanol used by the system will be cooled in the refrigerator 303 prior to being injected into the centrifugal separator(s) 304. The ethanol is injected from the alcohol tank 301 and/or the refrigerator 303 into the centrifugal separator(s) 304. Before, after, and/or simultaneously with injection of the ethanol into the centrifugal separator(s) 304, raw cannabis plant material is fed to the centrifugal separator(s) 304 via a hopper (not illustrated); most typically, a mass ratio of the solvent to the raw cannabis plant material in the centrifugal separator(s) 304 is about 5:1, but any suitable ratio may be used. The ethanol and cannabis plant material are fully mixed, most typically for between about 20 and about 40 minutes, to form a slurry, which is then centrifuged in the centrifugal separator(s) 304 to separate the slurry into a solid residue and a crude oil. It is to be expressly understood that one or more of the centrifugal separator(s) 304 may consist of a single mixing/centrifuging vessel, whereby the ethanol and cannabis plant material are slurried and subsequently centrifuged in the single mixing/centrifuging vessel, and/or one or more of the centrifugal separator(s) 304 may consist of multiple vessels, e.g. such that the ethanol and cannabis plant material are slurried in a first vessel of the centrifugal separator(s) 304 and the slurry is then transferred to and centrifuged in a second vessel of the centrifugal separator(s) 304.

One advantage of the present invention is that it permits the use of commercially available ethanol sources that may comprise a significant fraction of water. Particularly, the ethanol used in the system of the present invention, e.g. the alcohol present in the alcohol tank 301 and injected by the alcohol pump 302 into the centrifugal separator(s) 304, may, in embodiments, comprise up to about 8% water; it may be possible to use ethanol in which the water fraction is even higher. This feature greatly reduces the cost, and greatly increases the availability, of the ethanol solvent for use in the system.

Although not illustrated in FIG. 3, the cannabis plant material may, in embodiments, be subjected to various pre-processing steps before being fed to the centrifugal separator(s) 304. By way of non-limiting example, such pre-processing steps may include at least one of acceptability testing (e.g. for moisture content, contaminants, etc.) and size reduction (e.g. by chopping, cutting, grinding, shredding, etc.).

It is to be expressly understood that, in embodiments (like that illustrated in FIG. 3) in which two or more centrifugal separators 304 are present, the centrifugal separators 304 may be arranged in series, in parallel, or in a combination thereof. For example, in the embodiment illustrated in FIG. 3, the first and second centrifugal separators 304*a*,*b* are arranged in series; the ethanol solvent and the raw cannabis plant material are first fed to a first centrifugal separator 304*a*, where they are slurried and initially centrifuged, and the resulting liquor is then sent to a centrifugal separator 304*b*, where it is subjected to further separation by centrifugation. The centrifugal separation unit 300 may, but need not, comprise an impurity removal means, e.g. a filter, between successive centrifugal separators. Although not always necessary, in some embodiments in which centrifugal separator(s) 304 are arranged at least partially in series, as in the embodiment illustrated in FIG. 3, later and/or downstream centrifugal separator(s) may receive makeup ethanol from the ethanol tank 301 and/or the refrigerator 303.

Regardless of the number and arrangement of the centrifugal separator(s) 304, the centrifugal separation unit 300 produces two materials: a solid residue and a crude oil. The solid residue is generally "wet," i.e. comprising at least some residual ethanol and/or water, and the crude oil generally comprises compounds extracted from the cannabis plant material (e.g. cannabinoids and/or terpenes), solvent, and in many cases some residual solids. The solid residue is discarded (although it may in certain applications and embodiments be retained and optionally subjected to further processing), but the crude oil is then passed to the filter unit 400 illustrated in FIG. 4. In some embodiments, at least a portion of the solid residue and/or at least a portion of the crude oil is recycled to one or more centrifugal separator(s) 304.

Figure 4:
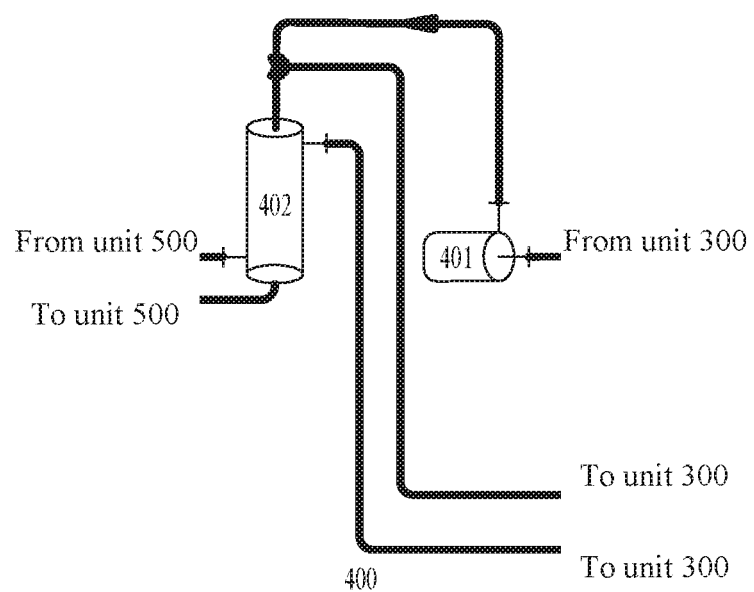
FIG. 4 is an illustration of a filter unit of a system for preparing a purified cannabis extract, according to embodiments of the present invention.

Referring now to FIG. 4, a filter unit 400 of a system for preparing a purified cannabis extract, according to embodiments of the present invention, comprises an optional pump 401 and a filter assembly 402. The pump 401 may be operable to supply at least a portion of the crude oil from the centrifugal separation unit 300 to the filter assembly at a desired pressure. The filter assembly 402 comprises a filter of any suitable type (e.g. hot filtration, cold filtration, vacuum filtration, etc.), any suitable filter medium (whether a surface filter, a depth filter, or both), and any suitable effective pore size. Upon passing through the filter assembly 402, whether directly from the centrifugal separation unit 300 or via the pump 401 (or both), the filtered crude oil is then passed to the concentration unit 500 illustrated in FIG. 5, although in some embodiments, as illustrated in FIGS. 3 and 4, a portion of the crude oil may be recycled from the filter assembly 402 back to the centrifugal separation unit 300.

Figure 5:
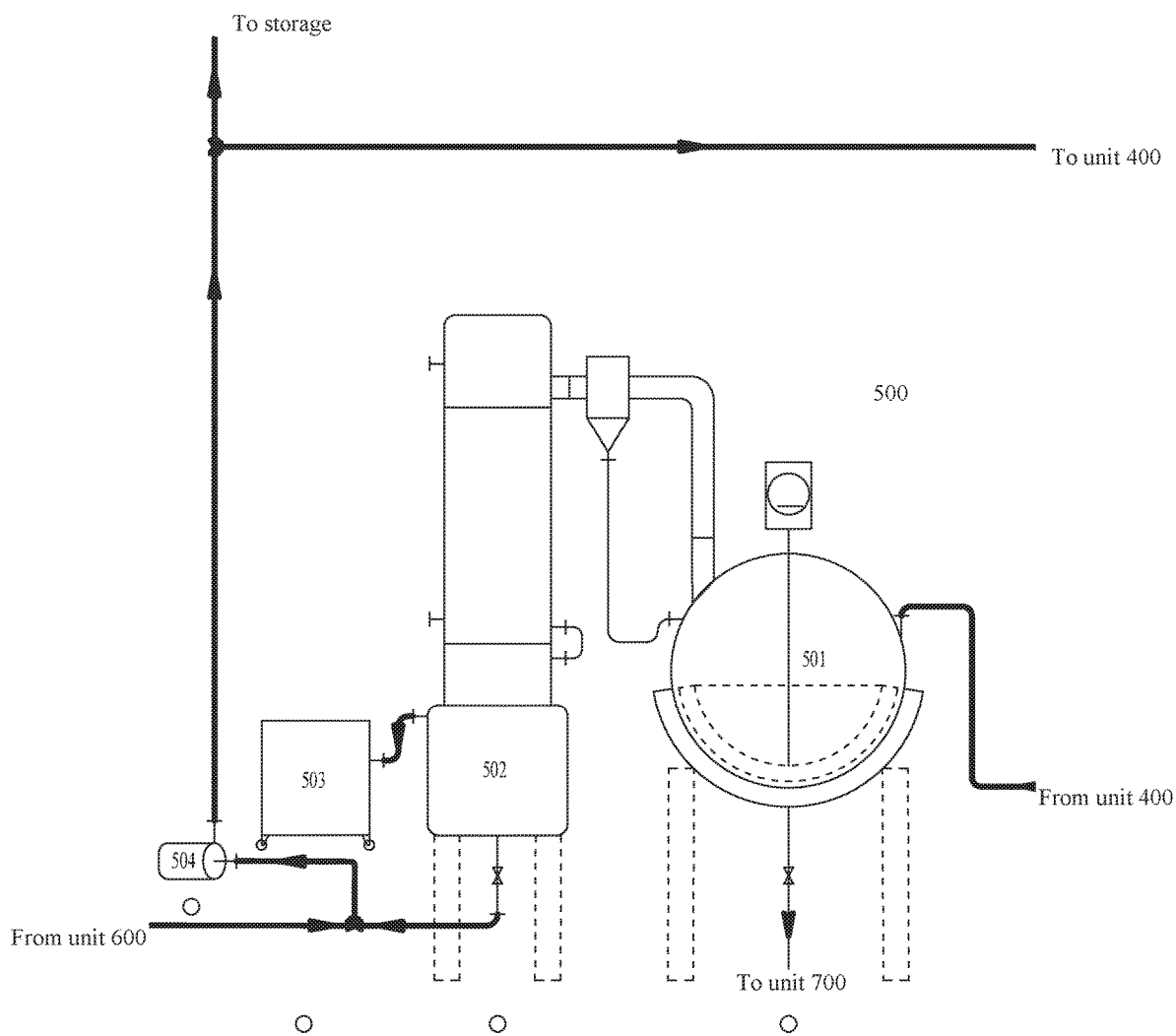
FIG. 5 is an illustration of a concentration unit of a system for preparing a purified cannabis extract, according to embodiments of the present invention.
Figure 10:
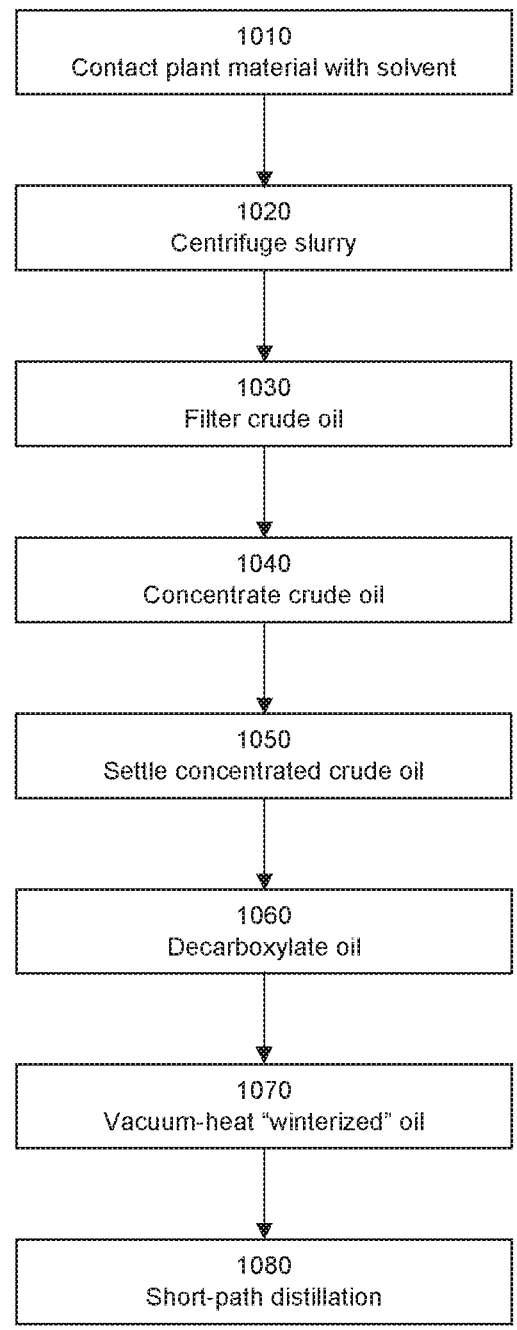
FIG. 10 is a process flow diagram of the comprehensive method for producing cannabis extract incorporating steps of contacting with solvent, centrifuging, filtering, concentrating, settling, decarboxylating, winterizing and short-path distillation.

Referring now to FIGS. 5 and 10, a concentration unit 500 of a system for preparing a purified cannabis extract, according to embodiments of the present invention, comprises a concentration evaporator 501, a cooler assembly 502, a vacuum pump 503, and a centrifugal pump 504. The filtered crude oil passes from the filter assembly 402 illustrated in FIG. 4 into the concentration evaporator 501, where it is heated to selectively evaporate the ethanol from the crude oil while leaving the compounds extracted from the cannabis plant material (e.g. cannabinoids and terpenes) in the liquid phase as a concentrated oil. In some, but by no means all, embodiments, the heating may be carried out under about atmospheric pressure. In some, but by no means all, embodiments, the heating may be to a temperature of between about 80 and about 90° C., or between about 90 and about 95° C. In some, but by no means all, embodiments, the heating may be carried out over a period of between about 10 and about 15 minutes, or between about 20 and about 25 minutes. In some, but by no means all, embodiments, the heating may be carried out in the presence of a catalyst. The concentration evaporator 501 may be any suitable type of evaporator, including but not limited to a circulation evaporator, a falling film evaporator, a rising film evaporator, a climbing and falling film plate evaporator, a multiple-effect evaporator, and/or an agitated thin film evaporator.

Figure 6:
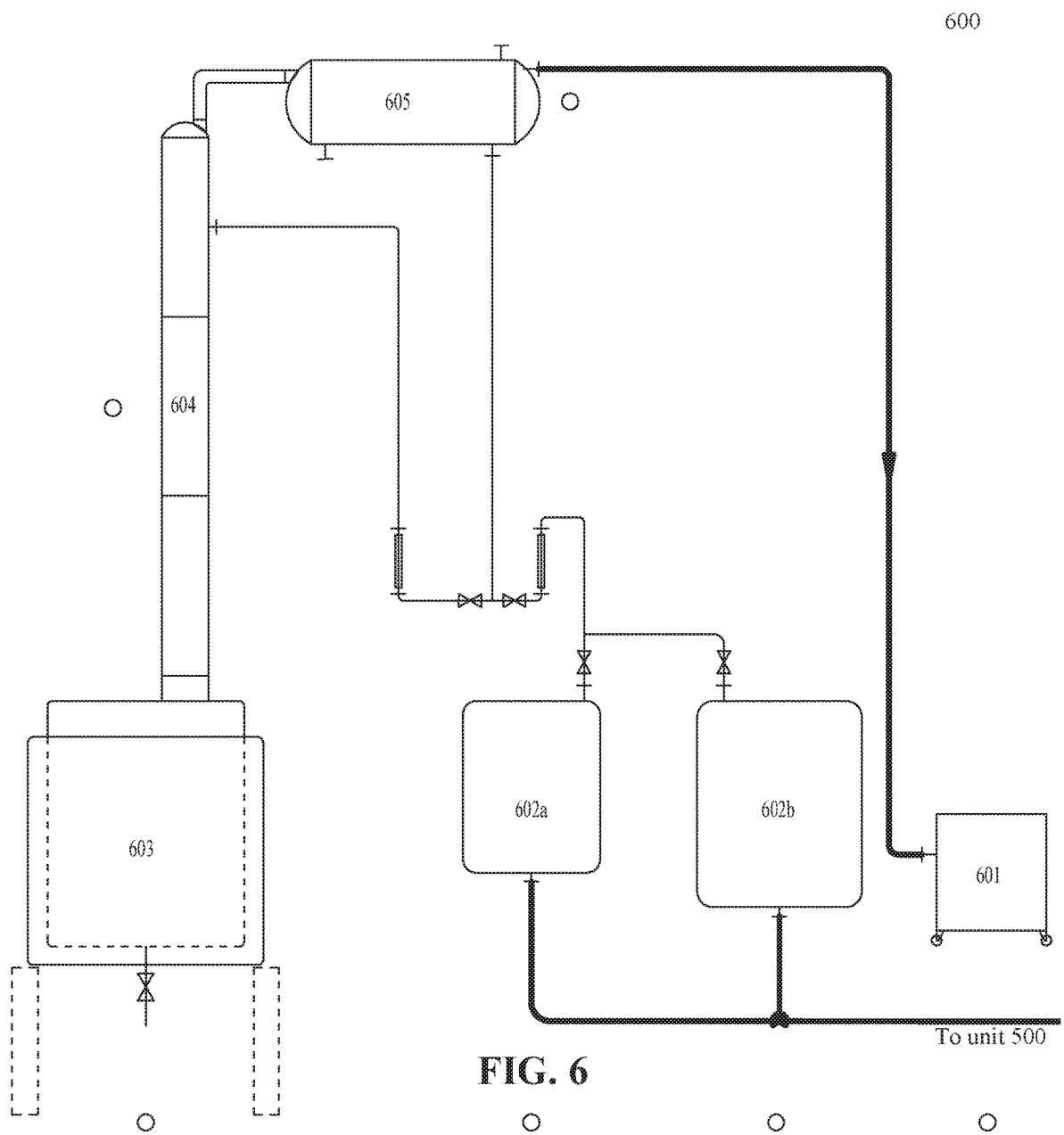
FIG. 6 is an illustration of a rectification unit of a system for preparing a purified cannabis extract, according to embodiments of the present invention.
Figure 7:
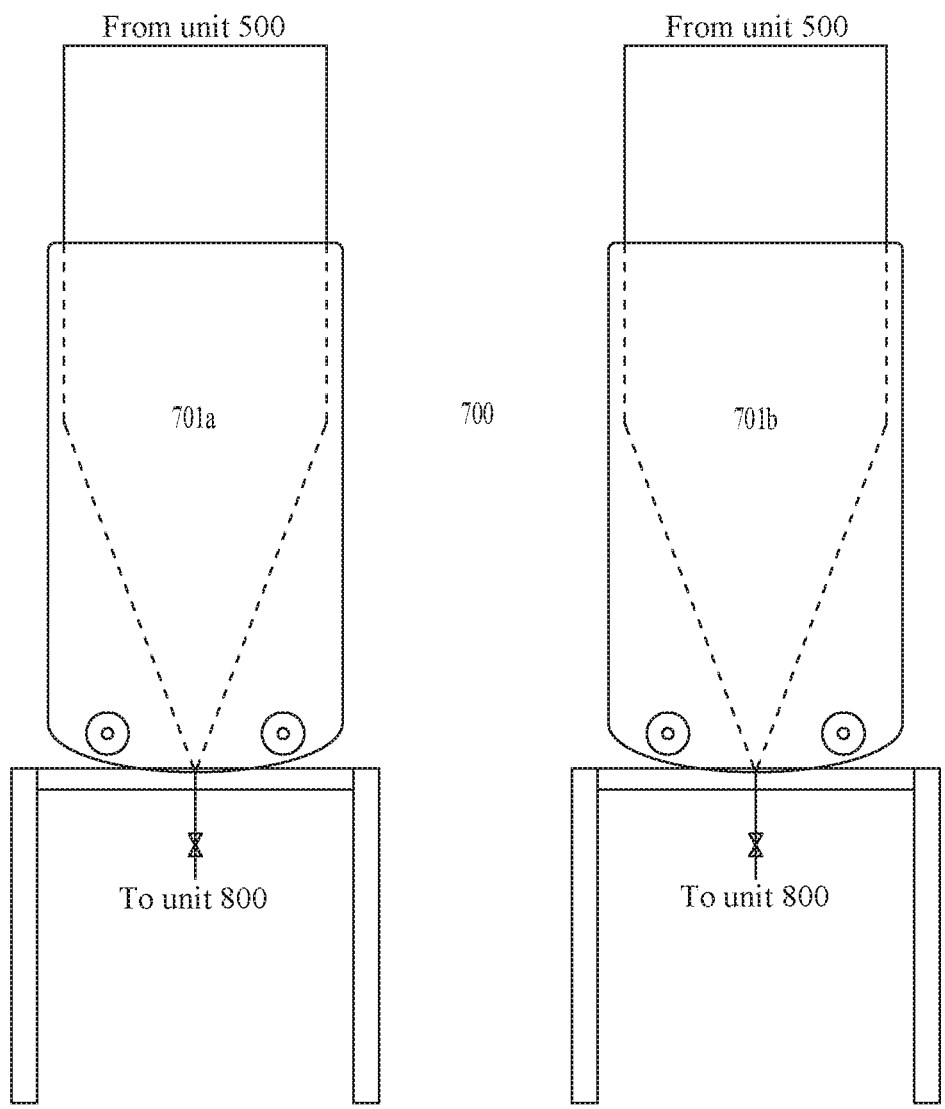
FIG. 7 is an illustration of a static separation unit of a system for preparing a purified cannabis extract, according to embodiments of the present invention.

As illustrated, the concentrated oil is sent from the concentration evaporator 501 to the static separation unit 700 illustrated in FIG. 7. The evaporated ethanol, which generally contains at least some impurities (e.g. water), is then condensed in the cooler assembly 502, which is maintained at sub-atmospheric pressure, and in some embodiments vacuum or near vacuum, by the vacuum pump 503. Upon collecting in a bottoms tank of the cooler assembly 502, the condensed ethanol may be pumped via centrifugal pump 504 to any one or more of the centrifugal separation unit 300 (e.g. to be immediately reused as part of the ethanol solvent for extraction of the desired compounds from the cannabis plant material), the filter unit 400 (e.g. to aid in filtration of the crude oil), to an ethanol storage tank that may be the same as or different from the alcohol tank 301 (e.g. if the ethanol is sufficiently pure after condensation to be stored for reuse), and the rectification unit 600 illustrated in FIG. 6 (e.g. to be further purified for use or reuse). Most typically, the ethanol collected in the cooler assembly 502 requires further purification and most or all of the ethanol is therefore passed to the rectification unit 600.

Referring now to FIG. 6, a rectification unit 600 of a system for preparing a purified cannabis extract, according to embodiments of the present invention, comprises a vacuum pump 601, optionally at least one storage tank 602 (in this case two storage tanks 602*a,b*), a rectification heater 603, a rectification column 604, and a cooler 605. The vacuum pump maintains at least one of the rectification heater 603, the rectification column 604, and the cooler 605 at sub-atmospheric pressure, and in some embodiments vacuum or near vacuum. The rectification heater 603 receives the impure ethanol condensed in the concentration unit 500 and heats the impure ethanol to cause the impurities to be separated in the rectification column 604; the impurities are collected in a bottoms and either discarded or further remediated in additional process units (not illustrated). In some, but by no means all, embodiments, the heating may be carried out under about atmospheric pressure. In some, but by no means all, embodiments, the heating may be to a temperature of between about 80 and about 90° C., or between about 90 and about 95° C. In some, but by no means all, embodiments, the heating may be carried out over a period of between about 10 and about 15 minutes, or between about 20 and about 25 minutes. In some, but by no means all, embodiments, the heating may be carried out in the presence of a catalyst.

Upon rectification, the now substantially pure ethanol is cooled in the cooler 605, optionally stored in one or more storage tanks 602, and recycled; generally, the rectified ethanol is recycled to the centrifugal separation unit 300, and particularly to the alcohol tank 301, to be reused as part of the ethanol extraction solvent, but may also be recycled to other process units, such as the filter unit 400 and/or the concentration unit 500.

Referring now to FIG. 7, a static separation unit 700 of a system for preparing a purified cannabis extract, according to embodiments of the present invention, comprises one or more settling tanks 701, in this case two settling tanks 701*a,b*. Generally, the settling tank(s) 701 receive crude oil from the concentration unit 500 via an inlet disposed at or near a top of the settling tank(s) 701, and the crude oil then remains in the settling tank(s) 701 for sufficient time to allow particulate impurities, which in embodiments may include plant debris, proteins, lipids, etc., to precipitate out of the crude oil. While the settling tank(s) 701 are depicted in FIG. 7 as conical settling tanks, it is to be expressly understood that any suitable settling device, such as an inclined plate settler or other device, may be used as a settling tank 701. After a predetermined residence time in the settling tank(s) 701, a sediment comprising the solid particulate impurities has formed and is removed and discarded, while the settled crude oil is passed to the decarboxylation and degassing unit 800 illustrated in FIG. 8.

In some (but by no means all) embodiments, static separation of the crude oil received from the concentration unit 500 may be aided by any one or more suitable means in the static separation unit 700 in addition to settling tank(s) 701. By way of first non-limiting example, the crude oil may be contacted with a solid separating agent and/or a liquid separating agent; in embodiments, a liquid separating agent may be a liquid (e.g. aqueous) solution or dispersion of a solid separating agent (e.g. a copper salt, a calcium salt, a sodium salt, a magnesium salt, silica, etc.). By way of second non-limiting example, the crude oil may be centrifuged. By way of third non-limiting example, the crude oil may be filtered.

Figure 8:
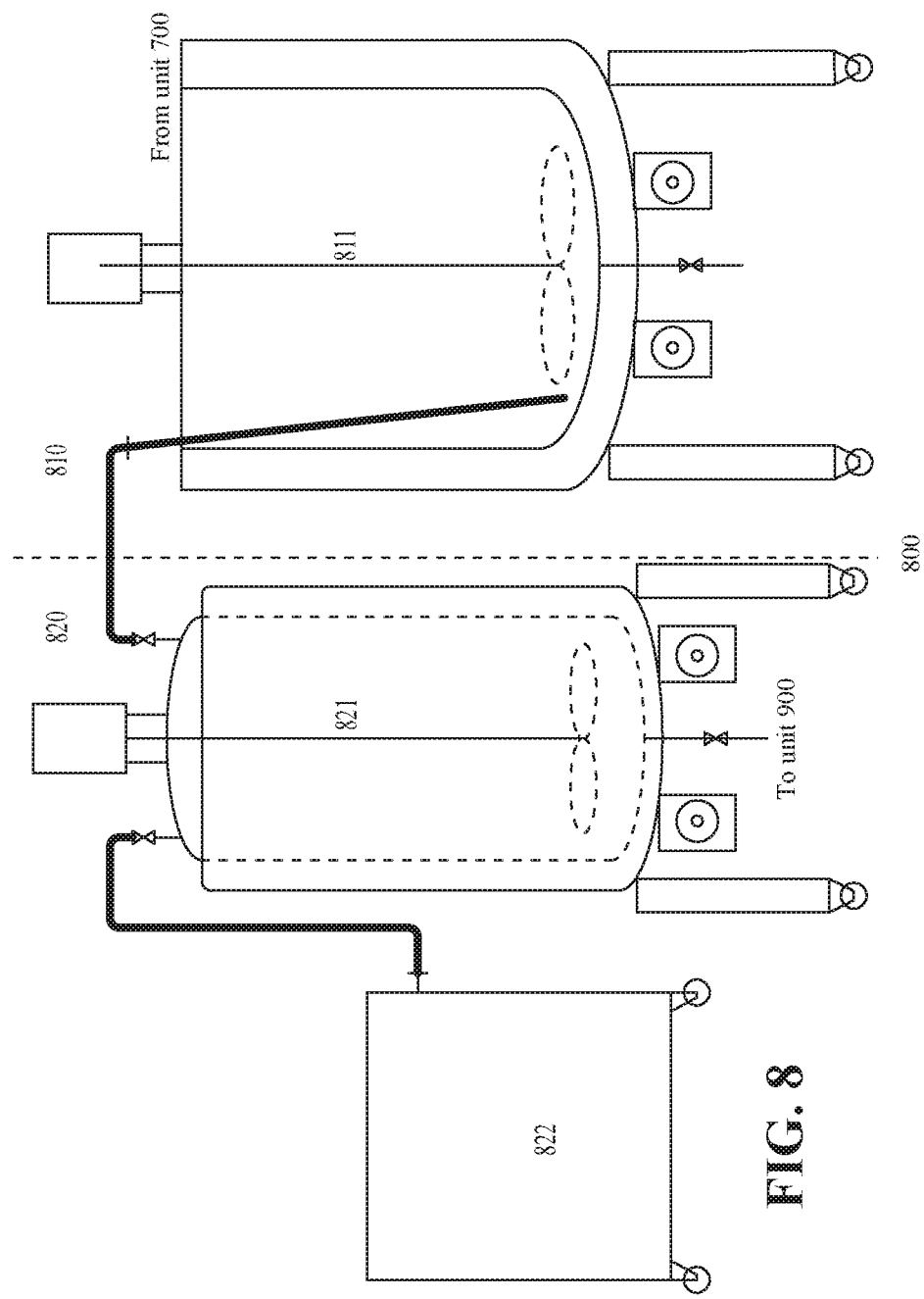
FIG. 8 is an illustration of a decarboxylation and degassing unit of a system for preparing a purified cannabis extract, according to embodiments of the present invention.

Referring now to FIG. 8, a decarboxylation and degassing unit 800 of a system for preparing a purified cannabis extract, according to embodiments of the present invention, comprises an atmosphere heating subunit 810 and a vacuum heating subunit 820. The atmosphere heating subunit 810 comprises an atmosphere heating vessel 811, which may optionally comprise an agitator, impeller, mixing paddle, or the like. The vacuum heating subunit 820 comprises a vacuum heating vessel 821, which may optionally comprise an agitator, impeller, mixing paddle, or the like, and a vacuum pump 822. The atmosphere heating vessel 811 receives the settled crude oil from the static separation unit 700 and heats the settled crude oil under approximately ambient or atmospheric pressure; this heating steps decarboxylates cannabinoids in the crude oil, which are often present in larger quantities in their carboxylated, i.e. carboxylic acid, forms (which are generally biologically inactive) than in their biologically active free or neutral forms. The heating of the crude oil in the atmosphere heating vessel 811 may, in some embodiments, also accomplish various "winterization" processes (i.e. removal of unwanted compounds) and may cause gases dissolved in the oil to be removed. In some, but by no means all, embodiments, the heating in the atmosphere heating vessel 811 may be carried out under about atmospheric pressure. In some, but by no means all, embodiments, the heating in the atmosphere heating vessel 811 may be to a temperature of between about 80 and about 90° C., or between about 90 and about 95° C. In some, but by no means all, embodiments, the heating in the atmosphere heating vessel 811 may be carried out over a period of between about 10 and about 15 minutes, or between about 20 and about 25 minutes. In some, but by no means all, embodiments, the heating in the atmosphere heating vessel 811 may take place in the presence of a catalyst.

Once decarboxylation is substantially complete, the vacuum heating vessel 821, which is maintained at a sub-atmospheric pressure (and in some embodiments vacuum or near-vacuum) by the vacuum pump 822, receives the decarboxylated oil from the atmosphere heating vessel 821 via a conduit. In the vacuum heating vessel 821, the decarboxylated oil is further heated under sub-atmospheric pressure as a preheating step before entering the short-path distillation unit 900 illustrated in FIG. 9; this preheating may, in some embodiments, assist in driving off gases dissolved in the oil.

In some embodiments, the decarboxylation and degassing unit 800 may be effective to convert substantially all of the carboxylated/carboxylic acid form of the compound of interest to the corresponding free or neutral form. By way of non-limiting example, the decarboxylation and degassing unit 800 may be effective to convert substantially all of the cannabidiolic acid present in the settled crude oil to cannabidiol.

Figure 9:
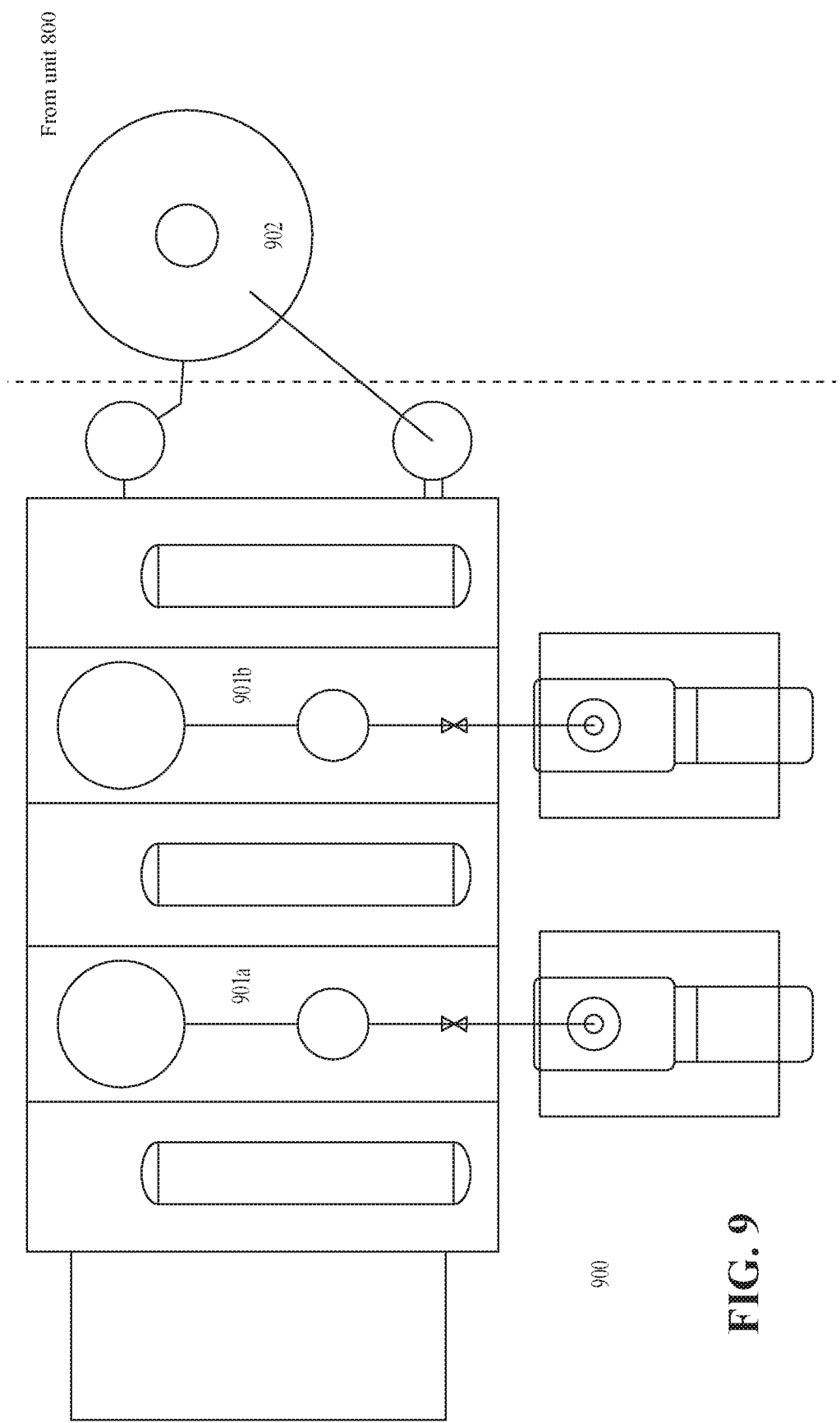
FIG. 9 is an illustration of a short-path distillation unit of a system for preparing a purified cannabis extract, according to embodiments of the present invention.

Referring now to FIG. 9, a short-path distillation unit 900 of a system for preparing a purified cannabis extract, according to embodiments of the present invention, comprises at least one short-path distillation apparatus 901, and in this embodiment two short path distillation apparatuses 901a,b. As known and described in the art, a short-path distillation apparatus is an apparatus in which the distillate travels a short distance, usually at sub-atmospheric pressure. Although not illustrated in detail in FIG. 9, each short-path distillation apparatus 901 comprises a still pot (in which the oil exiting the decarboxylation and degassing unit 800 is received), a vertical condenser (known as a "cold finger," and generally bent to direct the condensate), a cooling water flow path, a vacuum or gas inlet, and a distillate vessel in which the final product is collected. The advantages of short-path distillation are numerous, among which are that the distillation is carried out at lower temperature (thus decreasing the likelihood of oxidation or other degradation of temperature-sensitive constituents) and that equipment losses are smaller due to the shortened distances and smaller physical footprint of the distillation apparatus itself. It is to be expressly understood that, in embodiments in which the short-path distillation unit 900 comprises more than one short-path distillation apparatus 901, the short-path distillation apparatuses 901 may be disposed in series, in parallel (as in FIG. 9), or in any combined series/parallel arrangement.

As illustrated in FIG. 9, the short-path distillation unit 900 may optionally comprise a vacuum heater 902, which may be the same as or different from the vacuum heating vessel 821 of the decarboxylation and degassing unit 800. The vacuum heater 902 of the short-path distillation unit 900 heats the oil under sub-atmospheric (in some embodiments, vacuum or near-vacuum) pressures, which may serve any one or more of several purposes, including but not limited to further degassing of the oil and/or pre-treatment or pre-heating of the oil prior to entering the one or more short-path distillation apparatuses 901.

The finished product of the system described herein, obtained from the short-path distillation unit 900, is a yellow-colored or golden cannabinoid and/or terpene oil of high purity and quality. In embodiments, cannabinoids may make up at least about 70 wt %, and preferably at least about 80 wt %, of the end product. In some embodiments, cannabidiol may make up at least about 70 wt %, and preferably at least about 80 wt %, of the end product.

Referring now to FIG. 10, a method 1000 for preparing a purified cannabis extract is illustrated, according to embodiments of the present invention. In the embodiment illustrated in FIG. 10, the method 1000 comprises a contacting step 1010, a centrifugation step 1020, a filtration step 1030, a concentration step 1040, a settling step 1050, a decarboxylation step 1060, a vacuum heating step 1070, and a distilling step 1080.

In the contacting step 1010 of the method 1000, cannabis plant material is subjected to a solvent extraction process, particularly an ethanol extraction process, by being contacted with a liquid solvent (e.g. a mixture of ethanol and water). As a result of contacting step 1010, a raw extract or slurry is produced; the raw extract typically comprises the solvent, a compound or compounds of interest (e.g. cannabinoids and/or terpenes, including but not limited to cannabidiol), and proteins and/or lipids soluble in the solvent or a component thereof.

In the centrifugation step 1020 of the method 1000, the raw extract or slurry is centrifuged to produce a solid residue and a crude oil. The crude oil, comprising at least most of the solvent and compound or compounds of interest, is generally free of very large pieces of solid cannabis plant material, but may still contain smaller pieces.

In the filtration step 1030 of the method 1000, the crude oil is filtered by any suitable means to produce a filtered crude oil. At this point, the filtered crude oil is generally free of macroscopic plant matter, but may still contain dissolved or suspended solids, e.g., proteins and lipids.

In the concentration step 1040 of the method 1000, the solvent or a portion thereof (i.e. ethanol) is removed from the crude oil and optionally recycled to contacting step 1010 or another process step. Concentration step 1040 is generally accomplished by heating the filtered crude oil to selectively evaporate the ethanol solvent, which may then be condensed for recycle or removal. Removal and recovery of at least a portion of the solvent generally improves the efficiency of subsequent processing steps and results in a purer finished extract.

In the settling step 1050 of the method 1000, a sediment of solid particles is precipitated from the concentrated crude oil by any suitable means, although settling step 1050 generally comprises allowing the crude oil to reside for a predetermined period in a settling vessel, such as a conical settling tank or inclined plate settler. In embodiments, the settling of the sediment may be aided by any one or more of the addition of a chemical (solid or liquid) separating agent, centrifugation, filtration, and so on. Generally, a first phase resulting from settling step 1050 is a cannabinoid- and/or terpene-rich phase (e.g. comprising at least most, and in embodiments at least 75%, of cannabinoids and/or terpenes in the concentrated crude oil, and having a low proportion of proteins and/or lipids), and the second phase resulting from settling step 1050 is an impurity-rich phase (e.g. comprising at least most of the impurities in the concentrated crude oil and having a low proportion of substances of interest such as cannabinoids and/or terpenes); in embodiments, the impurities may include proteins and/or lipids. Typically, the first and second phases may be substantially immiscible to facilitate further processing.

In the decarboxylation step 1060 of the method 1000, the cannabinoid- and/or terpene-rich phase formed in settling step 1050 is decarboxylated by heating at approximately atmospheric or ambient temperature to form a "winterized" cannabinoid and/or terpene oil. The cannabinoid- and/or terpene-rich phase may, but need not, be agitated or stirred during decarboxylation step 1060.

In the vacuum heating step 1070 of the method 1000, the "winterized" cannabinoid and/or terpene oil is heated at sub-atmospheric (in some embodiments, vacuum or near-vacuum) pressures to further degas, purify, and/or pre-treat the oil and thereby form a distillation-ready oil. In some embodiments, the vacuum heating step 1070 may comprise more than one vacuum heating sub-step (e.g. by varying a temperature or pressure), in a single vessel or in two or more separate vessels.

In short-path distillation step 1080, the distillation-ready oil is distilled at least once in at least one short-path distillation apparatus to produce a finished cannabinoid and/or terpene oil. The finished product of the method 1000 is a yellow-colored or golden cannabinoid and/or terpene oil of high purity and quality. In embodiments, cannabinoids may make up at least about 70 wt %, and preferably at least about 80 wt %, of the end product. In some embodiments, cannabidiol may make up at least about 70 wt %, and preferably at least about 80 wt %, of the end product.

The method 1000 may optionally include any one or more additional steps not illustrated in FIG. 2. By way of non-limiting example, the solvent removed from the crude oil in concentration step 1040 may be rectified or otherwise purified and recovered.

Embodiments of the present invention may suitably be used to extract any one or more cannabinoids from cannabis or other plant material. Cannabinoids amenable to extraction by embodiments of the present invention include, but are not limited to, cannabichromene-type (CBC) cannabinoids, e.g. (±)-cannabichromene (CBC-$C_5$), (±)-cannabichromenic acid A (CBCA-$C_5$ A), (±)-cannabichromevarin (CBCV-$C_3$), and (±)-cannabichromevarinic acid A (CBCVA-$C_3$ A); cannabichromanone-type (CBCN) cannabinoids, e.g. cannabichromanone (CBCN-$C_5$), cannabichromanone-$C_3$ (CBCN-$C_3$), and cannabicoumaronone (CBCON-$C_5$); cannabidiol-type (CBD) cannabinoids, e.g. (−)-cannabidiol (CBD-$C_5$), cannabidiol monomethyl ether (CBDM-$C_5$), cannabidiol-$C_4$ (CBD-$C_4$), (−)-cannabidivarin (CBDV-$C_3$), cannabidiorcol (CBD-$C_1$), cannabidiolic acid (CBDA-$C_5$), and cannabidivarinic acid (CBDVA-$C_3$); cannabielsoin-type (CBE) cannabinoids, e.g. (5aS,6S,9R,9aR)-cannabielsoin (CBE-$C_5$), (5aS,6S,9R,9aR)-$C_3$-cannabielsoin (CBE-$C_3$), (5aS,6S,9R, 9aR)-cannabielsoic acid A (CBEA-$C_5$ A), (5aS,6S,9R,9aR)-cannabielsoic acid B (CBEA-$C_5$ B), (5aS,6S,9R,9aR)-$C_3$-cannabielsoic acid B (CBEA-$C_3$ B), cannabiglendol-$C_3$ (OH-iso-HHCV-$C_3$), dehydrocannabifuran (DCBF-$C_5$), and cannabifuran (CBF-$C_5$); cannabigerol-type (CBG) cannabinoids, e.g. cannabigerol ((E)-CBG-$C_5$), cannabigerol monomethyl ether ((E)-CBGM-$C_5$ A), cannabinerolic acid A ((Z)-CBGA-$C_5$ A), cannabigerovarin ((E)-CBGV-$C_3$), cannabigerolic acid A ((E)-CBGA-$C_5$ A), cannabigerolic acid A monomethyl ether ((E)-CBGAM-$C_5$ A), and cannabigerovarinic acid A ((E)-CBGVA-$C_3$ A); cannabicyclol-type (CBL) cannabinoids, e.g. (±)-(1aS,3aR,8bR,8cR)-cannabicyclol (CBL-$C_5$), (±)-(1aS,3aR,8bR,8cR)-cannabicyclolic acid A (CBLA-$C_5$ A), and (±)-(1aS,3aR,8bR,8cR)-cannabicyclovarin (CBLV-$C_3$); cannabinol-type (CBN) cannabinoids, e.g. cannabinol (CBN-$C_5$), cannabinol-$C_4$ (CBN-$C_4$), cannabivarin (CBN-$C_3$), cannabinol-$C_2$ (CBN-$C_2$), cannabiorcol (CBN-$C_1$), cannabinolic acid A (CBNA-$C_5$ A), and cannabinol methyl ether (CBNM-$C_5$); cannabinodiol-type (CBND) cannabinoids, e.g. cannabinodiol (CBND-$C_5$) and cannabinodivarin (CBND-$C_3$); cannabicitran-type or cannabitriol-type (CBT) cannabinoids, e.g. cannabicitran (CBT-$C_5$), (−)-(9R,10R)-trans-cannabitriol ((−)-trans-CBT-$C_5$), (+)-(9S,10S)-cannabitriol ((+)-trans-CBT-$C_5$), (±)-(9R,10S/9S,10R)-cannabitriol ((±)-cis-CBT-$C_5$), (−)-(9R,10R)-trans-10-O-ethyl cannabitriol ((−)-trans-CBT-OEt-$C_5$), (±)-(9R,10R/9S,10S)-cannabitriol-$C_3$ ((±)-trans-CBT-$C_3$), 8,9-dihydroxy-$\Delta^{6a(10a)}$-tetrahydrocannabinol (8,9-Di-OH-CBT-$C_5$), cannabidiolic acid A cannabitriol ester (CBDA-$C_5$ 9-OH-CBT-$C_5$ ester), cannabiripsol (cannabiripsol-$C_5$), (−)-6a,7,10a-trihydroxy-$\Delta^9$-tetrahydrocannabinol ((−)-cannabitetrol), and 10-oxo-$\Delta^{6a(10a)}$-tetrahydrocannabinol (OTHC); isocannabinoids, e.g. (−)-$\Delta^7$-trans-(1R,3R,6r)-isotetrahydrocannabinol, (±)-$\Delta^7$-1,2-cis-(1R,3R,6S/1S,3S,6R)-isotetrahydrocannabivarin, and (−)-$\Delta^7$-trans-(1R,3R,6R)-isotetrahydrocannabivarin; and tetrahydrocannabinol-type (THC) cannabinoids, e.g. $\Delta^9$-tetrahydrocannabinol ($\Delta^9$-THC-$C_5$), $\Delta^9$-tetrahydrocannabinol-$C_4$ ($\Delta^9$-THC-$C_4$), $\Delta^9$-tetrahydrocannabivarin ($\Delta^9$-THCV-$C_3$), $\Delta^9$-tetrahydrocannabiorcol ($\Delta^9$-THCO-$C_1$), $\Delta^9$-tetrahydrocannabinolic acid A ($\Delta^9$-THCA-$C_5$ A), $\Delta^9$-tetrahydrocannabinolic acid B ($\Delta^9$-THCA-$C_5$ B), $\Delta^9$-tetrahydrocannabinolic acid-$C_4$ A and/or B ($\Delta^9$-THCA-$C_4$ A and/or B), $\Delta^9$-tetrahydrocannabivarinic acid A ($\Delta^9$-THCVA-$C_3$ A), $\Delta^9$-tetrahydrocannabiorcolic acid A and/or B ($\Delta^9$-THCOA-$C_1$ A and/or B), (−)-$\Delta^8$-trans-(6aR,10aR)-$\Delta^8$-tetrahydrocannabinol ($\Delta^8$-THC-$C_5$), (−)-$\Delta^8$-trans-(6aR,10aR)-tetrahydrocannabinolic acid A ($\Delta^8$-THCA-$C_5$ A), and (−)-(6aS,10aR)-$\Delta^9$-tetrahydrocannabinol ((−)-cis-$\Delta^9$-THC-$C_5$).

Embodiments of the present invention may suitably be used to extract any one or more terpenes and terpenoids from cannabis or other plant material. Terpenes and terpenoids amenable to extraction by embodiments of the present invention include, but are not limited to, endo-borneol; δ-carene; bornyl acetate; α-ylangene; α-copaene; aromadendrene; eremophilene; longifolene; β-guaiene; valencene; β-bisabolene; γ-cadinene; β-selinene; neophytadiene; ferruginol; aristolone; β-amyrin; oleanane; ketoursene; α-amyrin; iridoids; iridoid glycosides; steroids, e.g. campesterol, β-sitosterol, γ-sitosterol, stigmasterol, tocopherols, cholesterol, testosterone, cholecalciferol, and ecdysone; hemiterpenoids, e.g. isoprene, prenol, and isovaleric acid; acyclic monoterpenes, e.g. ocimene and myrcenes; monocyclic monoterpenes, e.g. limonene, terpinene, phellandrene, and umbellulone; bicyclic monoterpenes, e.g. pinene α, pinene β, camphene, thujene, sabinene, and carene; acyclic monoterpenoids, e.g. linalool, citronellal, citral, citronellol, geraniol, and geranyl pyrophosphate; monocyclic monoterpenoids, e.g. grapefruit mercaptan, menthol, p-cymene, thymol, perillyl alcohol, and carvacrol; bicyclic monoterpenoids, e.g. camphor, borneol, eucalyptol, halomon, and ascaridole; sesquiterpenoids, e.g. farnesyl pyrophosphate, artemisinin, and bisabolol; diterpenoids, e.g. geranylgeranyl pyrophosphate, gibberellin, retinol, retinal, phytol, taxol, forskolin, aphidicolin, and salvinorin A; sesterterpenoids, e.g. geranylfarnesol; non-steroidal triterpenoids, e.g. saponins, squalene, lanosterol, oleanolic acid, ursolic acid, betulinic acid, and moronic acid); sesquarterpenes and sesquarterpenoids, e.g. ferrugicadiol and tetraprenylcurcumene; carotenes, e.g. α-carotene, β-carotene, γ-carotene, δ-carotene, lycopene, neurosporene, phytofluene, and phytoene; xanthophylls, e.g. canthaxanthin, cryptoxanthin, zeaxanthin, astaxanthin, lutein, and rubixanthin; polyterpenoids; norisoprenoids, e.g. 3-oxo-α-ionol, 7,8-dihydroionone, and precursors thereto; and activated isoprenes, e.g. isopentenyl pyrophosphate (IPP), dimethylallyl pyrophosphate (DMAPP), and precursors thereto.

A number of variations and modifications of the disclosure can be used. It would be possible to provide for some features of the disclosure without providing others. Additionally and/or alternatively, it may be possible to vary or modify the order and/or sequence of method steps or system processing units relative to the embodiments specifically described herein. Such modifications and variations are expressly contemplated to be within the scope of the present disclosure.

Ranges have been discussed and used within the forgoing description. One skilled in the art would understand that any sub-range within the stated range would be suitable, as would any number or value within the broad range, without deviating from the invention. Additionally, where the meaning of the term "about" as used herein would not otherwise be apparent to one of ordinary skill in the art, the term "about" should be interpreted as meaning within plus or minus five percent of the stated value.

Although the present disclosure describes components and functions implemented in the aspects, embodiments, and/or configurations with reference to particular standards and protocols, the aspects, embodiments, and/or configurations are not limited to such standards and protocols. Other similar standards and protocols not mentioned herein are in existence and are considered to be included in the present disclosure. Moreover, the standards and protocols mentioned herein and other similar standards and protocols not mentioned herein are periodically superseded by faster or more effective equivalents having essentially the same functions. Such replacement standards and protocols having the same functions are considered equivalents included in the present disclosure.

The present disclosure, in various aspects, embodiments, and/or configurations, includes components, methods, processes, systems and/or apparatus substantially as depicted and described herein, including various aspects, embodiments, configurations embodiments, subcombinations, and/or subsets thereof. Those of skill in the art will understand how to make and use the disclosed aspects, embodiments, and/or configurations after understanding the present disclosure. The present disclosure, in various aspects, embodiments, and/or configurations, includes providing devices and processes in the absence of items not depicted and/or described herein or in various aspects, embodiments, and/or configurations hereof, including in the absence of such items as may have been used in previous devices or processes, e.g., for improving performance, achieving ease and/or reducing cost of implementation.

The foregoing discussion has been presented for purposes of illustration and description. The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

Any of the steps, functions, and operations discussed herein can be performed continuously and automatically.

The invention claimed is:

1. A system for preparing a purified plant extract, comprising:
    a centrifugal separation unit, comprising at least one centrifugal separator, configured to receive solid plant material from a solid plant material source and a liquid solvent comprising ethanol from a separate solvent source, mix the solid plant material and the liquid solvent in the at least one centrifugal separator to form a slurry, and centrifuge the slurry in the at least one centrifugal separator to separate the slurry into a solid plant material residue and a raw extract, wherein the raw extract comprises at least one compound of interest and at least most of the liquid solvent;
    a filtration unit, comprising a filter assembly, configured to filter the raw extract to remove entrained solid plant material from the raw extract;
    a concentration unit, comprising an evaporator configured to receive the raw extract and heat the raw extract to remove at least most of the solvent therefrom by evaporation to thereby form a concentrated extract;
    a settling unit, comprising at least one settling vessel, configured to receive the concentrated extract and cause sedimentation of at least one impurity therefrom;
    a decarboxylation and degassing unit, comprising an atmosphere heating vessel and a vacuum heating vessel, wherein the atmosphere heating vessel is configured to receive the concentrated extract from the settling unit and heat the concentrated extract under approximately ambient or atmospheric pressure to decarboxylate at least a portion of the concentrated oil to form a decarboxylated oil, wherein the vacuum heating vessel is configured to directly receive the decarboxylated oil from the atmosphere heating vessel and heat the decarboxylated oil under sub-atmospheric pressure to form a winterized oil; and a short-path distillation unit, comprising at least one short-path distillation apparatus configured to receive the winterized oil from the decarboxylation and degassing unit and distill the winterized oil to form the purified plant extract.

2. The system of claim 1, wherein the solid plant material is a raw cannabis plant material.

3. The system of claim 1, wherein the at least one compound of interest comprises at least one cannabinoid or terpene.

4. The system of claim 3, wherein the at least one compound of interest comprises cannabidiol.

5. The system of claim 1, wherein a content of the at least one compound of interest in the purified plant extract is at least about 70% by weight.

6. The system of claim 1, wherein the liquid solvent consists essentially of (i) between about 92 and about 95 wt % ethanol and (ii) water.

7. The system of claim 1, wherein the at least one impurity comprises at least one protein or lipid.

8. The system of claim 1, further comprising a rectification unit, configured to receive evaporated solvent from the concentration unit and recover the solvent for recycle to at least one other unit of the system.

9. A method for preparing a purified plant extract, comprising:
(a) mixing, within at least one centrifugal separation unit, solid plant material received from a solid plant material source with a liquid solvent containing ethanol received from a separate solvent source to form a slurry;
(b) centrifuging, within the at least one centrifugal separation unit, the slurry to form a raw extract comprising at least one compound of interest and at least most of the liquid solvent;
(c) filtering the raw extract to remove entrained solid plant material from the raw extract;
(d) concentrating the raw extract by heating the raw extract to remove at least most of the solvent therefrom by evaporation to thereby form a concentrated extract;
(e) precipitating a sediment comprising at least one impurity from the concentrated extract;
(f) decarboxylating the concentrated extract by heating the concentrated extract under approximately ambient or atmospheric pressure in a first vessel to form a decarboxylated oil;
(g) heating the decarboxylated oil under sub-atmospheric pressure in a second, vacuumized vessel directly connected to the first vessel to form a winterized oil; and
(h) distilling the winterized oil by short-path distillation to form the purified plant extract.

10. The method of claim 9, wherein the solid plant material is a cannabis plant material.

11. The method of claim 9, wherein the at least one compound of interest comprises at least one cannabinoid or terpene.

12. The method of claim 11, wherein the at least one compound of interest comprises cannabidiol.

13. The method of claim 9, wherein a content of the at least one compound of interest in the purified plant extract is at least about 70% by weight.

14. The method of claim 9, wherein the liquid solvent consists essentially of (i) between about 92 and about 95 wt % ethanol and (ii) water.

15. The method of claim 9, wherein the at least one impurity comprises at least one protein or lipid.

16. The method of claim 9, further comprising rectifying the solvent evaporated in step (d) for recycle to at least one of steps (a), (b), and (c).

17. The method of claim 9, wherein a composition is produced from the purified plant extract which comprises at least about 70 wt % cannabinoids and terpenes and being substantially free of proteins and lipids.

18. The method of claim 17, wherein the produced composition comprises at least about 70 wt % cannabidiol.

19. The method of claim 18, wherein the produced composition is substantially free of cannabidiolic acid.

* * * * *